United States Patent
Fu et al.

(10) Patent No.: US 9,739,719 B2
(45) Date of Patent: Aug. 22, 2017

(54) MEASUREMENT SYSTEMS HAVING LINKED FIELD AND PUPIL SIGNAL DETECTION

(71) Applicant: KLA-Tencor Corporation, Milpitas, CA (US)

(72) Inventors: Jiyou Fu, Sunnyvale, CA (US); Noam Sapiens, Cupertino, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/927,753

(22) Filed: Oct. 30, 2015

(65) Prior Publication Data
US 2016/0123894 A1    May 5, 2016

Related U.S. Application Data

(60) Provisional application No. 62/073,693, filed on Oct. 31, 2014.

(51) Int. Cl.
*G01B 11/14* (2006.01)
*G01N 21/88* (2006.01)
(Continued)

(52) U.S. Cl.
CPC ..... *G01N 21/8851* (2013.01); *G01B 11/0616* (2013.01); *G01N 21/8806* (2013.01); *G01N 21/9501* (2013.01); *G01N 2021/8848* (2013.01)

(58) Field of Classification Search
CPC ........... G01N 21/8806; G01N 21/9501; G01N 21/95607; G01N 2021/479;
(Continued)

(56) References Cited

U.S. PATENT DOCUMENTS 5,608,526 A    3/1997    Piwonka-Corle et al.
5,859,424 A    1/1999    Norton et al.
(Continued)

FOREIGN PATENT DOCUMENTS

EP    1309875 A2    5/2003
WO    2014006614 A1    1/2014
(Continued)

OTHER PUBLICATIONS

International Search Report mailed on Feb. 17, 2016, for PCT Application No. PCT/US2015/058519 filed on Oct. 31, 2015 by KLA-Tencor Corporation, 3 pages.

*Primary Examiner* — Michael P Stafira
(74) *Attorney, Agent, or Firm* — Spano Law Group; Joseph S. Spano

(57) ABSTRACT

Methods and systems for simultaneous detection and linked processing of field signals and pupil signals are presented herein. In one aspect, estimates of one or more structural or process parameter values are based on field measurement signals, pupil measurement signals, or both. In addition, the quality of the measurements of the one or more structural or process parameter values is characterized based on the field measurement signals, pupil measurement signals, or both. In some embodiments, field measurement signals are processed to estimate one or more structural or process parameter values, and pupil measurement signals are processed to characterize the field measurement conditions. In some other embodiments, pupil measurement signals are processed to estimate one or more structural or process parameter values, and field measurement signals are processed to characterize the pupil measurement conditions.

20 Claims, 4 Drawing Sheets

(51) Int. Cl.
*G01B 11/06* (2006.01)
*G01N 21/95* (2006.01)

(58) Field of Classification Search
CPC ..... G01N 2021/8825; G01N 21/95623; G01N 2201/0697; G01N 2201/0826; G01N 2021/653; G01N 21/6445; G01N 21/6458; G01N 21/65; G01N 21/956
See application file for complete search history.

(56) References Cited

U.S. PATENT DOCUMENTS

| | | |
|---|---|---|
| 6,429,943 B1 | 8/2002 | Opsal et al. |
| 6,633,831 B2 | 10/2003 | Nikoonahad et al. |
| 6,734,967 B1 | 5/2004 | Piwonka-Corle et al. |
| 6,816,570 B2 | 11/2004 | Janik et al. |
| 6,895,075 B2 | 5/2005 | Yokhin et al. |
| 6,972,852 B2 | 12/2005 | Opsal et al. |
| 7,352,453 B2 | 4/2008 | Mieher et al. |
| 7,478,019 B2 | 1/2009 | Zangooie et al. |
| 7,502,101 B2 | 3/2009 | Raymond et al. |
| 7,715,019 B2 | 5/2010 | Kiers et al. |
| 7,826,071 B2 | 11/2010 | Shchegrov et al. |
| 7,929,667 B1 | 4/2011 | Zhuang et al. |
| 7,933,026 B2 | 4/2011 | Opsal et al. |
| 2006/0072105 A1 | 4/2006 | Wagner et al. |
| 2006/0273242 A1 | 12/2006 | Hunsche et al. |
| 2007/0035712 A1 | 2/2007 | Gassner et al. |
| 2009/0168039 A1* | 7/2009 | Kok .................... G03F 7/70075 355/67 |
| 2011/0043791 A1 | 2/2011 | Smilde et al. |
| 2011/0229830 A1 | 9/2011 | Bhattacharyya et al. |
| 2011/0249112 A1 | 10/2011 | Endo |
| 2011/0310388 A1 | 12/2011 | Hill et al. |
| 2012/0120396 A1 | 5/2012 | Kandel et al. |
| 2013/0114085 A1 | 5/2013 | Wang et al. |
| 2013/0229661 A1 | 9/2013 | Kandel et al. |
| 2014/0111791 A1 | 4/2014 | Manassen et al. |
| 2014/0172394 A1 | 6/2014 | Kuznetsov et al. |
| 2014/0222380 A1 | 8/2014 | Kuznetsov et al. |
| 2014/0297211 A1 | 10/2014 | Pandev et al. |
| 2014/0316730 A1 | 10/2014 | Shchegrov et al. |
| 2015/0042984 A1 | 2/2015 | Pandev et al. |
| 2015/0046118 A1 | 2/2015 | Pandev et al. |
| 2015/0293458 A1* | 10/2015 | Vanoppen ........... G03F 7/70558 355/53 |

FOREIGN PATENT DOCUMENTS

| | | |
|---|---|---|
| WO | 2014016056 A1 | 1/2014 |
| WO | 2014074873 A1 | 5/2014 |
| WO | 2014082938 A1 | 6/2014 |
| WO | 2014138741 A1 | 9/2014 |

* cited by examiner

MEASUREMENT SYSTEMS HAVING LINKED FIELD AND PUPIL SIGNAL DETECTION

CROSS REFERENCE TO RELATED APPLICATION

The present application for patent claims priority under 35 U.S.C. §119 from U.S. provisional patent application Ser. No. 62/073,693, entitled "Scatterometry With Linked Field Signal And Pupil Signal Detection System," filed Oct. 31, 2014, the subject matter of which is incorporated herein by reference in its entirety.

TECHNICAL FIELD

The described embodiments relate to metrology systems and methods, and more particularly to methods and systems for improved measurement of parameters characterizing the dimensions of structures generated by multiple patterning processes.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. Optical metrology techniques offer the potential for high throughput measurement without the risk of sample destruction. A number of optical metrology based techniques including scatterometry and reflectometry implementations and associated analysis algorithms are commonly used to characterize critical dimensions, film thicknesses, composition and other parameters of nanoscale structures.

Metrology applications involving the measurement of structures generated by semiconductor fabrication processes present challenges due to increasingly small resolution requirements, multi-parameter correlation, increasingly complex geometric structures, and increasing use of opaque materials. Thus, methods and systems for improved measurements are desired.

SUMMARY

Methods and systems for simultaneous detection and linked processing of field signals and pupil signals are presented herein. In one aspect, estimates of one or more structural or process parameter values are based on field measurement signals, pupil measurement signals, or both. In addition, the quality of the measurements of the one or more structural or process parameter values is characterized based on the field measurement signals, pupil measurement signals, or both. In some embodiments, field measurement signals are processed to estimate one or more structural or process parameter values, and pupil measurement signals are processed to characterize the field measurement conditions. In some other embodiments, pupil measurement signals are processed to estimate one or more structural or process parameter values, and field measurement signals are processed to characterize the pupil measurement conditions.

In one further aspect, both field and pupil measurement signals are simultaneously detected, and the detected signals are processed to estimate one or more structural or process parameter values and to adjust the focus position of the specimen under measurement.

In another further aspect, both field and pupil measurement signals are simultaneously detected, and the detected signals are processed to estimate one or more structural or process parameter values and to characterize asymmetry of the optical measurement system.

In another further aspect, both field and pupil measurement signals are simultaneously detected. The detected signals are processed to estimate one or more structural or process parameter values and to adjust an amount of illumination light directed to the pupil detector, the field detector, or both, without interacting with the specimen 107. In this manner, the intensity of the collected light is normalized.

In another further aspect, both field and pupil measurement signals are simultaneously detected. The detected signals are processed to estimate one or more structural or process parameter values and to identify the location in a direction parallel to the surface of the specimen under measurement relative to the optical system.

In another further aspect, both field and pupil measurement signals are simultaneously detected. The detected signals are processed to estimate one or more structural or process parameter values and to characterize measurement signal contamination. Examples of measurement signal contamination includes target noise, optical system imperfections such as aberration, stray light, etc., and relative motion between the optical system and the specimen under measurement, or any combination of these error sources.

In another further aspect, selectable illumination apertures and selectable collection apertures are configured to enable measurement of small pitch targets. More specifically, pupil signals selected for projection onto a pupil signal detector are derived from light diffracted from the illuminated measurement site at a diffraction order different from a zero diffraction order.

In another further aspect, both field and pupil measurement signals are simultaneously detected. The detected signals are iteratively processed to estimate one or more structural or process parameter values. More specifically, the value of the at least one structural or process parameter associated with the at least one measurement target is determined based on an iterative regression of the pupil measurement signals with a pupil measurement model and regression of the field measurement signals with a field measurement model.

In another further aspect, both field and pupil measurement signals are simultaneously detected. The detected signals are processed in a combined analysis to estimate one or more structural or process parameter values. In these examples, the measurement model is a combined measurement model that links structural parameters, material parameters, or a combination of structural and material parameters of the metrology target(s) for both pupil and field measurements.

The foregoing is a summary and thus contains, by necessity, simplifications, generalizations and omissions of detail;

DETAILED DESCRIPTION

Reference will now be made in detail to background examples and some embodiments of the invention, examples of which are illustrated in the accompanying drawings.

Methods and systems for simultaneous detection and linked processing of field signals and pupil signals are presented herein. In one aspect, both field and pupil measurement signals are simultaneously detected and processed to estimate one or more structural or process parameter values and to characterize the quality of the measurement. In some embodiments, field measurement signals are processed to estimate one or more structural or process parameter values, and pupil measurement signals are processed to characterize the field measurement conditions. In some other embodiments, pupil measurement signals are processed to estimate one or more structural or process parameter values, and field measurement signals are processed to characterize the pupil measurement conditions.

Field measurement signals are detected at or near the field plane of the measurement system. The field plane of the measurement system is conjugate to the surface of the specimen under measurement. Pupil plane measurement signals are detected at or near the pupil plane of the measurement system. The pupil plane is the Fourier transform of the field plane and is conjugate to the limiting aperture of the objective. In general, light reflected, diffracted, or scattered from different locations on the surface of a specimen under measurement is detected in different locations in the field plane of the measurement system, regardless of the collection angle. In contrast, light reflected, diffracted, or scattered at different angles from the surface of a specimen under measurement is detected in different locations in the pupil plane of the measurement system, regardless of the location of the light interaction on the surface of the specimen.

Figure 1:
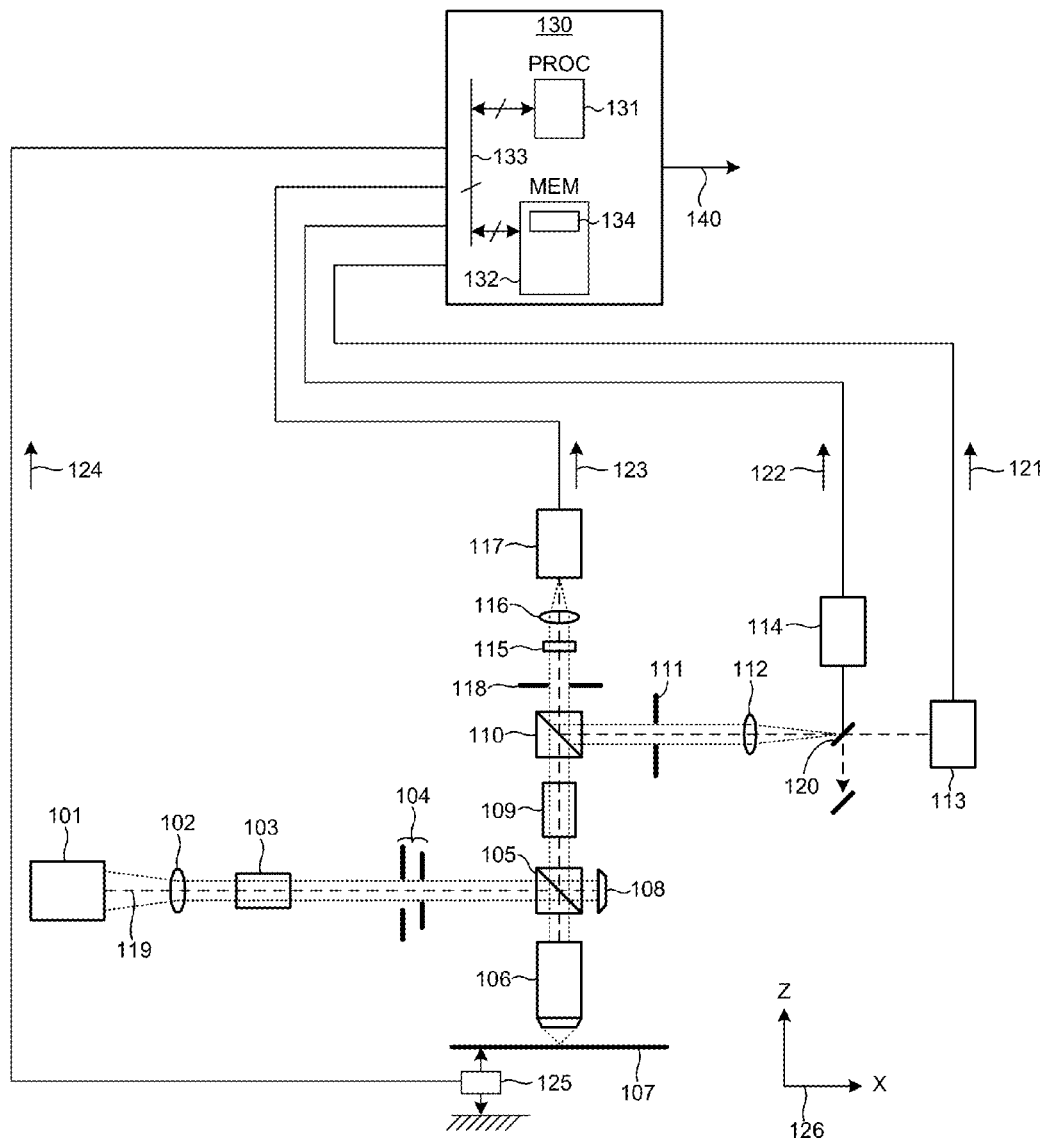
FIG. 1 illustrates a system 100 for measuring characteristics of a specimen in accordance with the exemplary methods presented herein.

FIG. 1 illustrates a system 100 for measuring characteristics of a specimen in accordance with the exemplary methods presented herein. As shown in FIG. 1, the system 100 may be used to perform simultaneous pupil and field measurements of one or more structures of a specimen 107. In this aspect, the system 100 may configured as a beam profile reflectometer (BPR) and a spectroscopic reflectometer (SR). Alternatively, system 100 may be configured as a BPR and a spectroscopic ellipsometer (SE). System 100 includes a high numerical aperture (NA) objective lens (e.g., NA>0.9) and at least one collection beam splitter 110 to generate an optical path to the pupil detector 117 and another optical path to the field detector 113 or 114. The field detector and pupil detector acquire field signals 121 or 122 and pupil signals 123, respectively, from specimen 107. The field signals and pupil signals are processed to estimate one or more structural or process parameter values and to characterize conditions of the parameter measurement. Exemplary measurement conditions include focus position, target position, intensity level, measurement asymmetry, signal contamination, etc.

As depicted in FIG. 1, system 100 includes an illumination source 101 that generates an amount of illumination light 119. In some embodiments, illumination source 101 is a broadband illumination source such as a xenon lamp, a laser driven light source, a multiple wavelength laser, a supercontinuum laser, etc. In some other embodiments, illumination source 101 includes a narrowband light source such as a single wavelength laser, a tunable narrowband laser, etc. In some embodiments, illumination source 101 includes a combination of broadband and narrowband illumination sources. In some embodiments, optical filters are included to select one or more illumination wavelength(s) and corresponding wavelength range(s).

As depicted in FIG. 1, illumination light 119 passes through illumination optics 102. Illumination optics 102 focus and collimate the illumination light. Illumination optics 102 include lens components, mirror components, or a combination of both. Illumination light passes through one or more selectable illumination apertures 104 before reaching illumination beam splitter 105. In some embodiments, the selectable illumination apertures 104 include a set of illumination field stops and a set of illumination pupil stops. The illumination field stops are configured to select the illumination spot size projected onto specimen 107. The illumination pupil stops are configured to select the illumination pupil projected onto specimen 107. The illumination field stops and pupil stops operate in conjunction with other illumination optics components (e.g., illumination optics 102 and objective 106) to achieve an illumination NA tuned for optimal light throughput, illumination field of view, and pupil on the surface of specimen 107. The aperture(s) of the selectable illumination apertures 104 may be formed by any suitable device including, but not limited to a mechanical pin-hole, a spatial light modulator (SLM), an apodizer, and any other beam forming and controlling component or sub-system.

Illumination beam splitter 105 directs a portion of the collimated illumination light to objective 106 and directs another portion of the collimated illumination light to intensity monitor 108. In some embodiments, intensity monitor 108 is communicatively coupled to computing system 130 and provides an indication of the overall illumination intensity, the illumination intensity profile, or both, to computing system 130. Objective 106 directs illumination light to the surface of specimen 107 over a broad range of angles of incidence. Light reflected, diffracted, and scattered from the surface of specimen 107 is collected by objective 106 and passes through collection beam splitter 110. A portion of the collected light is directed through a field detection path, while another portion of the collected light is directed through a pupil detection path. Illumination beam splitter 105 and collection beam splitter 110 may include any suitable beam splitting element including, but not limited to, a cubic beam splitter, a metallic coating plate, a dichroic optical coating plate, or other beam splitting mechanism.

The field detection path includes a selectable field collection aperture 111, focusing field optics 112, and at least one field detector. In some embodiments, the selectable field collection aperture 111 includes a set of field stops to select signals for projection onto field signal detectors 113 or 114. In some examples, higher order field signals are selected for projection onto field signal detectors 113 or 114. The aperture(s) of the selectable field collection aperture 111 may be formed by any suitable device including, but not limited to a mechanical pin-hole, a spatial light modulator (SLM), an apodizer, and any other beam forming and controlling component or sub-system.

In the embodiment depicted in FIG. 1, system 100 includes a field imaging detector 114 and a spectroscopic field detector 113. A flip-in mirror mechanism 120 is selectively located in the field detection path based on a command signal (not shown) received from computing system 130. In one configuration, flip-in mirror mechanism 120 is located in the field detection path and the collected light is directed to field imaging detector 114. In another configuration, flip-in mirror mechanism 120 is located outside the field detection path and the collected light is directed toward spectroscopic field detector 113. In this manner, system 100 is configured to perform either image-based or spectroscopic based field measurements.

In one embodiment, field imaging detector 114 is a vision camera that images the wafer surface onto the detector. By way of non-limiting example, the detected images may be used for overlay measurements, contrast based focus adjustment, and characterization of target noise. In one embodiment, spectroscopic field detector 113 is a spectrometer. By way of non-limiting example, the detected spectra may be used for measurement of critical dimensions (CD), thin film characterization, overlay measurement, focus adjustment based on zero order signals, optical system calibration and diagnosis, or any other suitable metrology.

The pupil detection path includes a selectable pupil collection aperture 118, a selectable narrow band pass filter 115, and pupil relay optics 116 that direct the collected light to pupil detector 117. In some embodiments, the selectable pupil collection aperture 118 includes a set of field stops to select signals for projection onto pupil signal detector 117. In some examples, higher order pupil signals are selected for projection onto pupil signal detector 117. The aperture(s) of the selectable pupil collection aperture 118 may be formed by any suitable device including, but not limited to a mechanical pin-hole, a spatial light modulator (SLM), an apodizer, and any other beam forming and controlling component or sub-system.

In the depicted embodiment, pupil detector 117 is an imaging detector. However, in some other embodiments, pupil detector 117 is a spectroscopic detector. In general, the pupil detection path may include one or more pupil detectors configured to collect pupil data simultaneously or sequentially. By way of non-limiting example, the detected pupil signals may be used for measurement of critical dimensions (CD), thin film characterization, overlay measurements, focus adjustment, optical system calibration and diagnosis, or any other suitable metrology.

In the embodiment depicted in FIG. 1, system 100 includes a polarizer 103 in the illumination path and an analyzer 109 in the collection path. Depending on whether polarizer 103 is rotating or not, system 100 may be configured to perform spectroscopic reflectometry (SR) measurements or spectroscopic ellipsometry (SE) measurements. In this manner, system 100 may be selectively configured to perform SR or SE measurements.

In addition, system 100 includes a measurement device (e.g., encoder 125) configured to measure the position of specimen 107 relative to the optical system in the direction perpendicular to the surface of specimen 107 (i.e., z-direction depicted in coordinate frame 126). In this manner, encoder 125 provides an indication of the focus position of specimen 107 relative to the optical system. Pupil signals 123 and field signals 121 or 122 can be collected simultaneously along with an indication of focus position 124 for analysis by computing system 130.

In one further aspect, both field and pupil measurement signals are simultaneously detected. The detected signals are processed to estimate one or more structural or process parameter values and to adjust the focus position of the specimen under measurement.

In one example, an imaging detector is employed to perform pupil image measurements (e.g., pupil imaging detector 117) and an imaging detector is employed to simultaneously perform field image measurements (e.g., field imaging detector 114). When the focus position of specimen 107 is changed, the pupil image collected by a pupil imaging detector changes significantly in size and shape for a high NA system, such as system 100. While acquiring field image signals 122, computing system 130 acquires pupil image signals 123. Based on the pupil image signals 123, computing system 130 determines the pupil image size, shape, and intensity distribution to estimate the focus position of specimen 107. Based on the estimate of focus position, computing system 130 communicates command signals to either a wafer positioning system (not shown) or an optical positioning system (not shown) to adjust the focus position of specimen 107 relative to the optical system. In this manner, the focus position of specimen 107 is monitored and adjusted during field image acquisition based on pupil image data.

In some other examples, the focus position is evaluated based on pupil image signals while moving the focus position of specimen 107 incrementally or continuously in the z-direction.

In another further aspect, both field and pupil measurement signals are simultaneously detected. The detected signals are processed to estimate one or more structural or process parameter values and to characterize asymmetry of the optical measurement system.

In one example, an imaging detector is employed to perform pupil image measurements (e.g., pupil imaging detector 117) and an imaging detector is employed to simultaneously perform field image measurements (e.g., field imaging detector 114). Depending on the desired parameter to be measured, both field and pupil images of one or more known film specimens or grating specimens are collected for a series of different z-positions. For each z-position, computing system 130 determines the intensity distribution of the collected field and pupil images. Asymmetrical non-uniformities of the measured intensity distribution are mapped for both pupil and field images. In some examples, the relation between pupil images and field images is mapped as a function of focus position. Correction tables or functions are generated by computing system 130 to correct asymmetries present in field images and pupil images based on the measured field images and pupil images. During measurement of unknown specimens, pupil images, field images, or both, are corrected based on the correction tables or functions.

In another further aspect, both field and pupil measurement signals are simultaneously detected. The detected signals are processed to estimate one or more structural or process parameter values and to adjust an amount of illumination light directed to the pupil detector, the field detector, or both, without interacting with the specimen 107. In this manner, the intensity of the collected light is normalized.

In one example, an imaging detector is employed to perform pupil image measurements (e.g., pupil imaging detector 117) and an imaging detector is employed to simultaneously perform field image measurements (e.g., field imaging detector 114). While acquiring field image signals 122, computing system 130 acquires pupil image signals 123. Based on the pupil image signals 123, computing system 130 determines the pupil image contrast. Based on the measured contrast, computing system 130 communicates command signals to a portion of the illumination subsystem (not shown) to adjust an amount of light directed to the pupil detector, the field detector, or both, to normalize the light detected at each detector.

In another further aspect, both field and pupil measurement signals are simultaneously detected. The detected signals are processed to estimate one or more structural or process parameter values and to identify the location in a direction parallel to the surface of the specimen under measurement relative to the optical system.

In some examples, field images acquired, for example, by field imaging detector 114, are processed by computing system 130 to identify the boundary of the measurement target with sub-pixel accuracy. Based on the identified boundary, computing system 130 determines the center of the measurement target. During overlay measurement, the estimate of target location is employed to select particular pixel signals for analysis and reduce the required target placement accuracy and corresponding alignment effort. During CD measurements and thin film measurements, the estimate of target location is employed to determine whether the measurement target is centered within the placement tolerance. If not, the associated pupil images are marked with the location offset determined based on the field images. Based on the measured location offset, computing system 130 communicates command signals, for example, to a wafer positioning system, to reposition specimen 107 in any of the x and y directions, and locate the measurement target within the placement tolerance.

In another further aspect, both field and pupil measurement signals are simultaneously detected and processed to estimate one or more structural or process parameter values and to characterize measurement signal contamination such as target noise. In some embodiments, pupil signals are acquired to estimate one or more structural or process parameter values, while field signals are acquired to evaluate signal contamination that arises from the measurement target itself, optical system imperfections such as aberration, stray light, etc., relative motion between the optical system and the specimen under measurement (i.e., undesired x, y, or z movements), or any combination of these error sources. In some other embodiments, field signals are acquired to estimate one or more structural or process parameter values, while pupil signals are acquired to evaluate the aforementioned measurement error sources.

For imaging examples, contrast and image uniformity can be used to estimate target noise. In one example, BPR pupil measurements are performed to measure overlay and image based field measurements are performed simultaneously to characterize target noise such as edge roughness, image contrast to characterize pad to pad variability, or the combination of edge roughness and image contrast. Based on the results of the field image analysis, a computing system 130 determines whether the error associated with the corresponding pupil measurements exceeds a predetermined threshold. If the measurement error is estimated to exceed the predetermined threshold value, computing system 130 communicates an error message that can be read by a user of system 100 to call attention to the identified measurements.

In some examples, spectroscopic field signals acquired, for example, by spectroscopic field detector 113, are processed by computing system 130 to estimate one or more structural or process parameter values, while pupil signals acquired, for example, by pupil imaging detector 117, are processed by computing system 130 to characterize measurement signal contamination.

In one example, SR/SE signals acquired by spectroscopic field detector 113 are processed by computing system 130 to estimate CD or thin film parameter values, while BPR imaging signals are acquired by pupil imaging detector 117 to characterize measurement signal contamination. In this example, a broadband illumination source (e.g., a laser driven light source) is employed. Illumination optics 103 and illumination apertures 104 are selected to achieve a 15 micrometer spot size projected onto the surface of specimen 107. In the collection path of the field signal path, selectable pupil aperture 111 is configured to select a collection NA range (e.g., NA=0.05). If polarizer 103 does not rotate during data acquisition, spectroscopic reflectometer signals are collected by detector 113. If polarizer 103 is rotating during data acquisition, spectroscopic ellipsometry signals are collected by detector 113. The collected field signals 121 are processed by computing system 130 to determine CD or thin film parameter values, for example, by regression of a measurement model. A selectable narrow band pass filter 115 is located in the pupil detection path. In some examples, the narrow band pass filter is configured to pass collected light in a range of 20-50 nanometers, centered for example at 685 nanometers or 330 nanometers. In general, the specific wavelength range is selected to either avoid or select higher diffraction orders in the pupil image. The pupil image signals 123 are processed by computing system 130 to determine target noise, optical system imperfections, relative motion, or any combination thereof, based on the acquired pupil images.

In another example, SR/SE signals acquired by spectroscopic field detector 113 are processed by computing system 130 to characterize measurement signal contamination, while BPR imaging signals are acquired by pupil imaging detector 117 to estimate CD or thin film parameter values. In this example, narrowband illumination (e.g., 2~5 nm wavelength range) is provided to the specimen 107 by opening a shutter of a narrowband laser illumination source or by inserting narrowband filter(s) in the illumination path. The selectable illumination aperture 104 is adjusted to project a 5 micrometer spot size on the surface of specimen 107. The field lens 112 is adjusted to high magnification to spread the resulting field image over at least 50 pixels. The pupil signals 123, the field signals 121, and the z-encoder signals 124 are acquired simultaneously. The pupil image signals 123 are processed by computing system 130 to determine CD or thin film parameter values. The field signals 121 are processed by computing system 130 to determine target noise, optical system imperfections, relative motion, or any combination thereof, based on the acquired spectroscopic field signals.

In general, simultaneously detected field and pupil measurement signals can be processed to estimate one or more structural or process parameter values and adjust the focus position of the specimen under measurement, characterize asymmetry of the optical measurement system, characterize measurement signal contamination, identify the location of the specimen under measurement relative to the optical system, or any combination thereof.

In one embodiment, system 100 includes both BPR and SR modules as described hereinbefore; combining both imaging and scatterometry measurement functionality in the same tool. System 100 utilizes simultaneously detected field and pupil signals to estimate structural parameter values and adjust focus position and measurement target location as described hereinbefore. In this manner, system 100 does not require dedicated auto-focus and pattern recognition modules to perform these operations.

In another further aspect, the selectable illumination apertures 104 and the selectable collection aperture 111 are configured to enable measurement of small pitch targets. More specifically, the pupil signals selected for projection onto pupil signal detector 117 are derived from light diffracted from the illuminated measurement site at a diffraction order different from a zero diffraction order.

Figure 2:
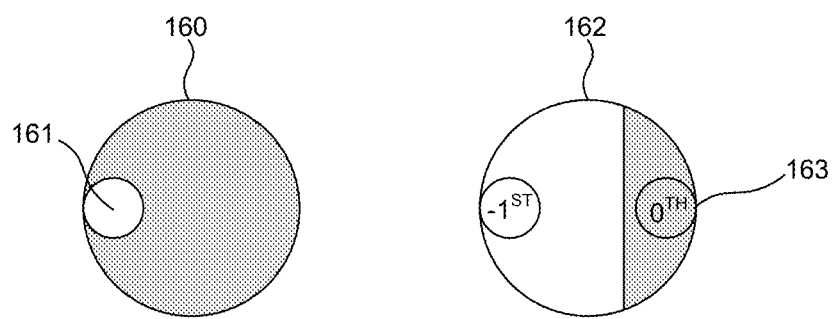
FIG. 2 depicts an exemplary illumination aperture 160 and collection aperture 162 for a set of measurements.
Figure 3:
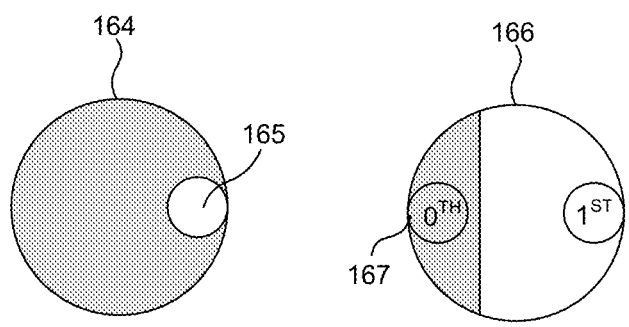
FIG. 3 depicts an exemplary illumination aperture 164 and collection aperture 166 for another set of measurements.

FIG. 2 depicts an exemplary illumination aperture 160 and collection aperture 162 for a first set of measurements. As depicted in FIG. 2, selectable illumination aperture 104 is configured such that the illumination 161 is located at the edge of the pupil while the selectable collection aperture 111 is configured to block 0th order light 163, while enabling −1st order diffracted light to pass through. FIG. 3 depicts an exemplary illumination aperture 164 and collection aperture 166 for a second set of measurements. In this example, selectable illumination aperture 104 is configured such that the illumination 165 is located at the opposite edge of the pupil as illumination 161. Meanwhile the selectable collection aperture 111 is configured to block 0th order light 167, while enabling 1st order diffracted light to pass through. In this manner, a scatterometric measurement (e.g. BPR) can be performed in the field plane, the pupil plane, or both. Locating the illumination to the side of the pupil enables the use of the entire pupil. Measurements of features having smaller pitch is enabled since the distance of the −1st order diffracted light and the 1st order diffracted light in the pupil is inversely proportional to the target pitch. Furthermore, since the distance between the 0th order diffracted light and the +/−1st order diffracted light is directly proportional to the incident light wavelength, targets with relatively small pitch can be measured with longer wavelength illumination light. This enables measurement of layers where short wavelength light is unable to penetrate. Since the light separation in the pupil is complete, an illumination that includes vertical poles and a collection that includes horizontal blocks may be used to measure y targets. Moreover, these illumination and collection schemes may be combined to perform simultaneous measurements of gratings in the x and y directions. The shapes of the illumination provided in the aforementioned illustration are provided by way of non-limiting example. In general, other illumination and collection shapes may be contemplated within the scope of this patent document.

In another further aspect, both field and pupil measurement signals are simultaneously detected. The detected signals are iteratively processed to estimate one or more structural or process parameter values. More specifically, the value of the at least one structural or process parameter associated with the at least one measurement target is determined based on an iterative regression of the pupil measurement signals with a pupil measurement model and regression of the field measurement signals with a field measurement model.

In one embodiment, computing system 130 determines an estimate of a CD parameter based on pupil image signals 123 and determines an estimate of a film stack parameter (e.g., film thickness) based on spectroscopic field signals 121 in an iterative regression analysis.

In this example, the CD measurement model includes a parameterization of the metrology target in terms of the CD parameter of interest. In addition, the CD measurement model includes a parameterization of the measurement tool itself (e.g., wavelengths, angles of incidence, polarization angles, etc.). Similarly, the film stack measurement model includes a parameterization of the metrology target in terms of the film stack parameter of interest (e.g., film thickness). In addition, the film stack measurement model includes a parameterization of the measurement tool itself. In addition, simulation approximations (e.g., slabbing, Rigorous Coupled Wave Analysis (RCWA), etc.) are carefully performed to avoid introducing excessively large errors. Discretization and RCWA parameters are defined.

Machine parameters ($P_{machine}$) are parameters used to characterize the metrology tool itself. Exemplary machine parameters include angle of incidence (AOI), analyzer angle (A0), polarizer angle (P0), illumination wavelength, numerical aperture (NA), etc. Specimen parameters ($P_{specimen}$) are parameters used to characterize the geometric and material properties of the specimen. For a thin film specimen, exemplary specimen parameters include refractive index, dielectric function tensor, nominal layer thickness of all layers, layer sequence, etc.

For measurement purposes, the machine parameters of the multi-target model are treated as known, fixed parameters and the specimen parameters of the measurement model, or a subset of specimen parameters, are treated as unknown, floating parameters. The floating parameters are resolved by a fitting process (e.g., regression, library matching, etc.) that produces the best fit between theoretical predictions and measured data. The unknown specimen parameters, $P_{specimen}$, are varied and the model output values are calculated until a set of specimen parameter values are determined that results in a close match between the model output values and the measured values.

In an iterative regression analysis, computing system 130 fits measured pupil signals to the CD measurement model to arrive at an estimated CD parameter value. The film stack parameters present in the CD measurement model are floated during this regression. Then computing system 130 fits the measured spectroscopic field signals to the film stack model to arrive at an estimated film stack parameter value (e.g., film thickness). The CD parameter values present in the film stack model are fixed to the values determined by the previous regression of pupil signals to the CD measurement model. Subsequently, computing system 130 again fits the measured pupil signals to the CD measurement model to arrive at an updated estimate of the CD parameter value. At this iteration, the film stack parameters present in the CD measurement model are fixed to the values determined by the previous regression of the spectroscopic field signals to the film stack model. This iteration continues until the parameter estimates reach sufficient accuracy.

In another further aspect, both field and pupil measurement signals are simultaneously detected. The detected signals are processed in a combined analysis to estimate one or more structural or process parameter values. In these examples, the measurement model is a combined measurement model that links structural parameters, material parameters, or a combination of structural and material parameters of the metrology target(s) for both pupil and field measurements.

Figure 4:
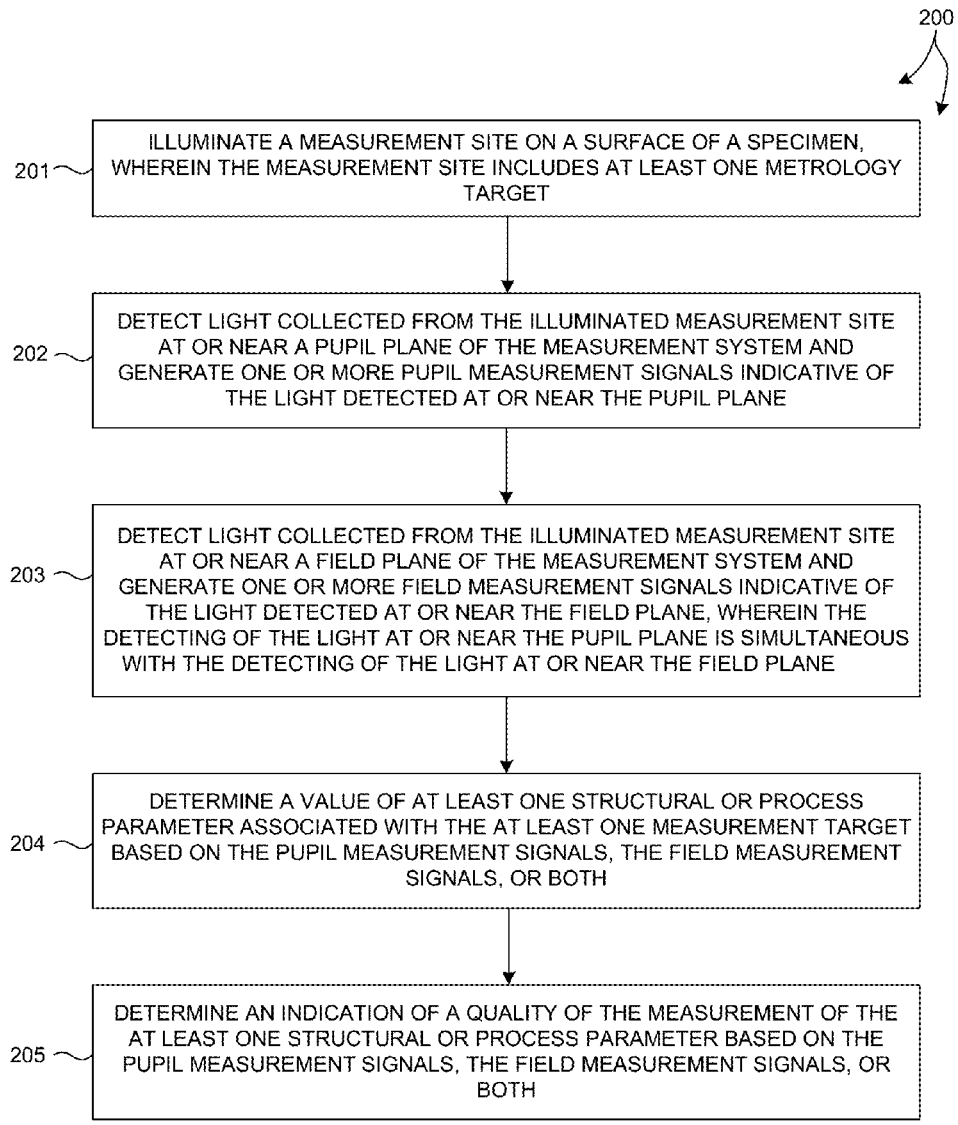
FIG. 4 is a flowchart illustrative of a method 200 suitable for implementation by a metrology system such as metrology system 100 illustrated in FIG. 1 of the present invention.

FIG. 4 illustrates a method 200 suitable for implementation by a metrology system such as metrology system 100 illustrated in FIG. 1 of the present invention. In one aspect, it is recognized that data processing blocks of method 200 may be carried out via a pre-programmed algorithm executed by one or more processors of computing system 130, or any other general purpose computing system. It is recognized herein that the particular structural aspects of metrology system 100 do not represent limitations and should be interpreted as illustrative only.

In block 201, a measurement site on a surface of a specimen is illuminated by an illumination system (e.g., illuminator 101). The measurement site includes at least one metrology target.

In block 202, light collected from the illuminated measurement site is detected at or near a pupil plane of the measurement system. In addition, one or more pupil measurement signals (e.g., pupil signals 123) indicative of the light detected at or near the pupil plane are generated by a pupil detector (e.g., pupil detector 117).

In block 203, light collected from the illuminated measurement site is detected at or near a field plane of the measurement system. The detecting of the light at or near the pupil plane is simultaneous with the detecting of the light at or near the field plane. In addition, one or more field measurement signals (e.g., field measurement signals 121 or 122) indicative of the light detected at or near the field plane are generated by a field detector (e.g., field detector 114 or 113).

In block 204, a value of at least one structural or process parameter associated with the at least one measurement target is determined by computing system 130 based on the pupil measurement signals, the field measurement signals, or both.

In block 205, an indication of a quality of the measurement of the at least one structural or process parameter is determined by computing system 130 based on the pupil measurement signals, the field measurement signals, or both.

In an optional block, the structural or process parameter value is stored in a memory (e.g., memory 132).

As depicted in FIG. 1, system 100 includes multiple measurement technologies (i.e., BPR and SR or SE). However, in general, system 100 may include any number of different measurement technologies. By way of non-limiting example, system 100 may be configured as a spectroscopic ellipsometer (including Mueller matrix ellipsometry), a spectroscopic reflectometer, a spectroscopic scatterometer, an overlay scatterometer, an angular resolved beam profile reflectometer, a polarization resolved beam profile reflectometer, a beam profile reflectometer, a beam profile ellipsometer, any single or multiple wavelength ellipsometer, or any combination thereof.

In a further embodiment, system 100 may include one or more computing systems 130 employed to perform measurements in accordance with the methods described herein. The one or more computing systems 130 may be communicatively coupled to the detectors of system 100. In one aspect, the one or more computing systems 130 are configured to receive measurement data associated with measurements of the structure of specimen 107.

It should be recognized that the various steps described throughout the present disclosure may be carried out by a single computer system 130 or, alternatively, a multiple computer system 130. Moreover, different subsystems of the system 100, such as the scatterometer and the beam profile reflectometer, may include a computer system suitable for carrying out at least a portion of the steps described herein. Therefore, the aforementioned description should not be interpreted as a limitation on the present invention but merely an illustration. Further, the one or more computing systems 130 may be configured to perform any other step(s) of any of the method embodiments described herein.

In addition, the computer system 130 may be communicatively coupled to the detectors of system 100 in any manner known in the art. For example, the one or more computing systems 130 may be coupled to computing systems associated with the detectors of system 100. In another example, the detectors may be controlled directly by a single computer system coupled to computer system 130.

The computer system 130 of the metrology system 100 may be configured to receive and/or acquire data or information from the subsystems of the system (e.g., detectors 113, 114, and 117, and the like) by a transmission medium that may include wireline and/or wireless portions. In this manner, the transmission medium may serve as a data link between the computer system 130 and other subsystems of the system 100.

Computer system 130 of system 300 may be configured to receive and/or acquire data or information (e.g., measurement results, modeling inputs, modeling results, etc.) from other systems by a transmission medium that may include wireline and/or wireless portions. In this manner, the transmission medium may serve as a data link between the computer system 130 and other systems (e.g., memory on-board metrology system 100, external memory, or other external systems). For example, the computing system 130 may be configured to receive measurement data from a storage medium (i.e., memory 132 or an external memory) via a data link. For instance, spectral measurement results obtained using spectrometer 113 may be stored in a permanent or semi-permanent memory device (e.g., memory 132 or an external memory). In this regard, the spectral results may be imported from on-board memory or from an external memory system. Moreover, the computer system 130 may send data to other systems via a transmission medium. For instance, a parameter value 140 determined by computer system 130 may be communicated and stored in an external memory. In this regard, measurement results may be exported to another system.

Computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 134 implementing methods such as those described herein may be transmitted over a transmission medium such as a wire, cable, or wireless transmission link. For example, as illustrated in FIG. 1, program instructions 134 stored in memory 132 are transmitted to processor 131 over bus 133. Program instructions 134 are stored in a computer readable medium (e.g., memory 132). Exemplary computer-readable media include read-only memory, a random access memory, a magnetic or optical disk, or a magnetic tape.

Figure 5:
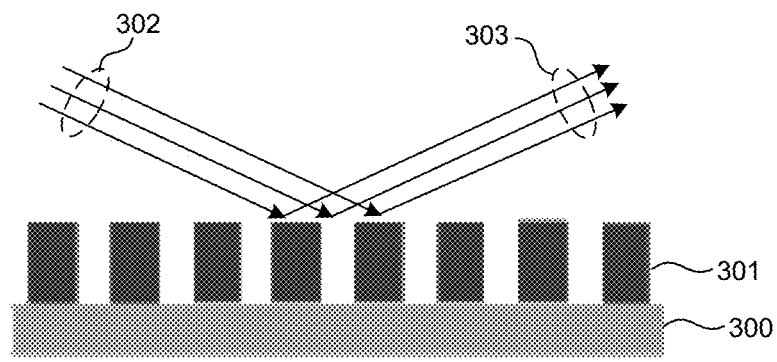
FIG. 5 depicts a patterned layer 301 disposed over an underlayer 300 of a semiconductor wafer. In the depicted embodiment, the patterned layer 301 is a grating structure having uniform pitch.

FIG. 5 depicts a patterned layer 301 disposed over an underlayer 300 of a semiconductor wafer. In the depicted embodiment, the patterned layer 301 is a grating structure having uniform pitch. In addition, oblique illumination light 302 is incident on patterned layer 301, and light 303 is diffracted from patterned layer 301. When the grating structure of patterned layer 301 is perfectly uniform, as depicted in FIG. 5, the light diffracted from patterned layer 301 is zero order diffracted light only. Thus, for an ideal structure constructed by a multiple patterning process (ΔCD=0 and pitch walk=0), only $0^{th}$ diffraction order is present for all angles of incidence and wavelengths available for optical scatterometry.

Figure 6:
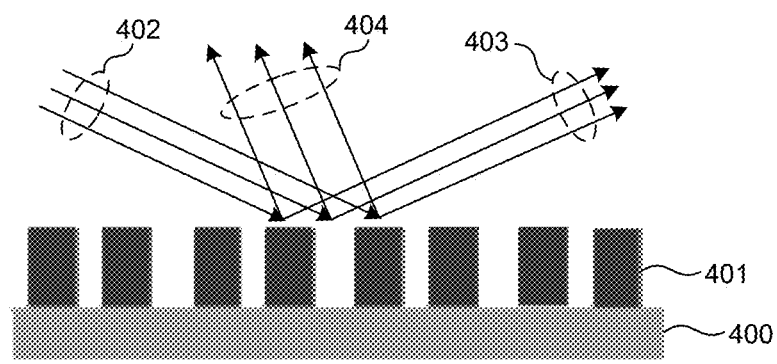
FIG. 6 depicts a patterned layer 401 disposed over an underlayer 400 of a semiconductor wafer. In the depicted embodiment, the patterned layer 401 is a grating structure having non-uniform pitch.

FIG. 6 depicts a patterned layer 401 disposed over an underlayer 400 of a semiconductor wafer. In the depicted embodiment, the patterned layer 401 is a grating structure having non-uniform pitch. In addition, oblique illumination light 402 is incident on patterned layer 401. When the grating structure of patterned layer 401 is non-uniform, as depicted in FIG. 6, the light diffracted from patterned layer 401 includes multiple diffraction orders. Multiple patterning errors create grating patterns having non-uniform pitch. Hence, the effective unit cell of these patterns is much larger as well as the structure period. This enables higher diffraction orders (e.g., first order or negative first order) to become propagating. As depicted in FIG. 6, the light diffracted from non-uniform patterned layer 401 includes zero order diffracted light 403 and first order diffracted light 404. Depending on the sign convention employed, first order diffracted light 404 may be considered diffracted light having a grating order of one or negative one.

Typical semiconductor metrology, such as spectroscopic ellipsometry, involves the collection and analysis of zero order diffracted light. However, in another aspect, diffracted light having a diffraction order different from zero is collected and analyzed to determine the value of at least one structural parameter that is indicative of a geometric error induced by a multiple patterning process. In some embodiments, a single diffraction order different from zero (e.g., −1 or 1) is collected and analyzed to determine the value of at least one structural parameter that is indicative of a geometric error induced by a multiple patterning process.

The relation between the angle of incidence and the 0th order angle is given by equation (1), where $\theta_{AOI}$ is the angle of incidence of the illumination light and $\theta_{0th}$ is the angle of the 0th order.

$$\theta_{AOI} = -\theta_{0th} \quad (1)$$

The numerical aperture of the $-1^{st}$ order is related to the numerical aperture of the $0^{th}$ order, the wavelength of the illumination light, λ, and the pitch of the grating structure, P, as given by equation (2).

$$NA_{-1st} = NA_{0th} - \frac{\lambda}{P} \quad (2)$$

In some other embodiments, solid immersion techniques may be employed to include light diffracted at higher order (i.e., any order different from zero) within the pupil of the system. In this manner, the same detector may be employed to detect both zero order diffracted light and higher order diffracted light, even for systems without a large collection NA.

In yet another further aspect, short wavelength components of the illumination beam are employed to highlight whether a structure is periodic based on the response of the structure to short wavelength illumination. Sufficiently short illumination wavelengths enable the capture of first order diffraction elements that would otherwise be evanescent. In general, it is desirable to reduce the wavelengths associated with the illumination light as much as possible to enhance measurement sensitivity for small pitch structure. Hence, in some embodiments, vacuum ultraviolet illumination light may be desireable.

In some embodiments, it may be desireable to employ apertures to separate collected light according to diffraction order, i.e. separate "0" and "−1" order in collection. If illumination and collection modes are such that "0" and "−1" orders overlap and interfere, it may be desireable to implement beam scanning over the grating to evaluate fringe visibility and determine the strength of the 1st order.

In general, detection of higher order diffracted light does not have to be in the pupil plane; wafer plane measurements could also be implemented.

In a further aspect, measurement data from multiple targets is collected for measurements. In some examples, the use of measurement data associated with multiple targets eliminates, or significantly reduces, the effect of under layers in the measurement result. In one example, measurement signals from two targets are subtracted to eliminate, or significantly reduce, the effect of under layers in each measurement result. The use of measurement data associated with multiple targets increases the sample and process information embedded in the model.

In another further aspect, measurement data from both measurement targets and assist targets that may be found on-device or within scribe lines is collected for measurements.

In some examples, the measurement methods described herein are implemented as an element of a SpectraShape® optical critical-dimension metrology system available from KLA-Tencor Corporation, Milpitas, Calif., USA.

In some other examples, the measurement methods described herein are implemented off-line, for example, by a computing system implementing AcuShape® software available from KLA-Tencor Corporation, Milpitas, Calif., USA.

In another example, the methods and systems described herein may be applied to overlay metrology. Grating measurements are particularly relevant to the measurement of overlay. The objective of overlay metrology is to determine shifts between different lithographic exposure steps. Performing overlay metrology on-device is difficult due to the small size of on-device structures, and the typically small overlay value.

For example, the pitch of typical scribe line overlay metrology structures varies from 200 nanometers to 2,000 nanometers. But, the pitch of on-device, overlay metrology structures is typically 100 nanometers or less. In addition, in a nominal production environment, the device overlay is only a small fraction of the periodicity of the device structure. In contrast, proxy metrology structures used in scatterometry overlay are frequently offset at larger values, e.g., quarter of the pitch, to enhance signal sensitivity to overlay.

Under these conditions, overlay metrology is performed with sensor architectures having sufficient sensitivity to small offset, small pitch overlay. The methods and systems described herein may be employed to obtain a measurement signal sensitive to overlay based on on-device structures, proxy structures, or both.

In general, the methods and systems for performing semiconductor metrology presented herein may be applied directly to actual device structures or to dedicated metrology targets (e.g., proxy structures) located in-die or within scribe lines.

In yet another aspect, the measurement results described herein can be used to provide active feedback to a process tool (e.g., lithography tool, etch tool, deposition tool, etc.). For example, values of the structural or process parameters determined using the methods described herein can be communicated to a lithography tool to adjust the lithography system to achieve a desired output (e.g., focus and dosage). In a similar way etch parameters (e.g., etch time, diffusivity, etc.) or deposition parameters (e.g., time, concentration, etc.) may be included in a measurement model to provide active feedback to etch tools or deposition tools, respectively.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including measurement applications such as critical dimension metrology, overlay metrology, focus/dosage metrology, and composition metrology. However, such terms of art do not limit the scope of the term "metrology system" as described herein. In addition, the metrology system 100 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A system comprising:
   an illumination source configured to illuminate a measurement site on a surface of a specimen, wherein the measurement site includes at least one metrology target;
   a first detector configured to detect light collected from the illuminated measurement site at or near a pupil plane of the measurement system and generate one or more pupil measurement signals indicative of the light detected at or near the pupil plane;

a second detector configured to detect light collected from the illuminated measurement site at or near a field plane of the measurement system and generate one or more field measurement signals indicative of the light detected at or near the field plane; and a computing system configured to:
receive the pupil measurement signals and the field measurement signals;
determine a value of at least one structural or process parameter associated with the at least one measurement target based on the pupil measurement signals, the field measurement signals, or both; and
determine an indication of a quality of the measurement of the at least one structural or process parameter based on the pupil measurement signals, the field measurement signals, or both.

2. The system of claim 1, wherein the indication of the quality of the measurement of the at least one structural or process parameter is any of an indication of a focus position, an indication of a target position, an indication of an illumination intensity level, an indication of a measurement asymmetry, and an indication of a signal contamination.

3. The system of claim 2, wherein the computing system is further configured to:
communicate a command signal to adjust a location of the specimen in a direction parallel to the surface of the specimen in response to the indication of the target position.

4. The system of claim 2, wherein the computing system is further configured to:
communicate a command signal to adjust an illumination intensity based on the indication of the intensity level.

5. The system of claim 2, wherein the computing system is further configured to:
calibrate a measurement asymmetry based on the indication of the measurement asymmetry.

6. The system of claim 2, wherein the computing system is further configured to:
communicate an error flag in response to the indication of signal contamination.

7. The system of claim 1, further comprising:
a measurement device configured to measure a position of the specimen in a direction perpendicular to the surface of the specimen.

8. The system of claim 7, wherein the computing system is further configured to:
communicate a command signal to adjust a focus position of the specimen based on the indication of the position of the specimen in the direction perpendicular to the surface of the specimen.

9. The system of claim 1, wherein the determining of the value of the at least one structural or process parameter associated with the at least one measurement target is based on an iterative regression of the pupil measurement signals with a pupil measurement model and regression of the field measurement signals with a field measurement model.

10. The system of claim 1, wherein the estimate of the one or more structural or process parameter values is based on the field measurement signals and the indication of the measurement quality is based on the pupil measurement signals.

11. The system of claim 1, wherein the estimate of the one or more structural or process parameter values is based on the pupil measurement signals and the indication of the measurement quality is based on the field measurement signals.

12. The system of claim 1, wherein the first amount of detected light is diffracted from the illuminated measurement site at a diffraction order different from a zero diffraction order.

13. The system of claim 1, wherein the one or more structural or process parameters associated with the at least one measurement target include any of a critical dimension, a thin film dimension, an overlay measurement, a lithography focus, and a lithography dosage.

14. The system of claim 1, wherein the first and second detectors are configured to detect the amount of light at multiple wavelengths, multiple collection angles, or a combination of multiple wavelengths and multiple collection angles.

15. A method comprising:
illuminating a measurement site on a surface of a specimen, wherein the measurement site includes at least one metrology target;
detecting light collected from the illuminated measurement site at or near a pupil plane of the measurement system;
generating one or more pupil measurement signals indicative of the light detected at or near the pupil plane;
detecting light collected from the illuminated measurement site at or near a field plane of the measurement system, wherein the detecting of the light at or near the pupil plane is simultaneous with the detecting of the light at or near the field plane;
generating one or more field measurement signals indicative of the light detected at or near the field plane;
determining a value of at least one structural or process parameter associated with the at least one measurement target based on the pupil measurement signals, the field measurement signals, or both; and
determining an indication of a quality of the measurement of the at least one structural or process parameter based on the pupil measurement signals, the field measurement signals, or both.

16. The method of claim 15, wherein the indication of the quality of the measurement of the at least one structural or process parameter is any of an indication of a focus position, an indication of a target position, an indication of an illumination intensity level, an indication of a measurement asymmetry, and an indication of a signal contamination.

17. A measurement system comprising:
an illumination source configured to illuminate a measurement site on a surface of a specimen, wherein the measurement site includes at least one metrology target;
a first detector configured to detect light collected from the illuminated measurement site at or near a pupil plane of the measurement system and generate one or more pupil measurement signals indicative of the light detected at or near the pupil plane;
a second detector configured to detect light collected from the illuminated measurement site at or near a field plane of the measurement system and generate one or more field measurement signals indicative of the light detected at or near the field plane; and
a non-transient computer readable medium comprising instructions that when executed by a processor cause the processor to:
receive the pupil measurement signals and the field measurement signals;
determine a value of at least one structural or process parameter associated with the at least one measurement target based on the pupil measurement signals, the field measurement signals, or both; and determine an indication of a quality of the measurement of the at least one structural or process parameter based on the pupil measurement signals, the field measurement signals, or both.

18. The measurement system of claim 17, wherein the indication of the quality of the measurement of the at least one structural or process parameter is any of an indication of a focus position, an indication of a target position, an indication of an illumination intensity level, an indication of a measurement asymmetry, and an indication of a signal contamination.

19. The measurement system of claim 17, wherein the determining of the value of the at least one structural or process parameter associated with the at least one measurement target is based on an iterative regression of the pupil measurement signals with a pupil measurement model and regression of the field measurement signals with a field measurement model.

20. The measurement system of claim 17, wherein the first amount of detected light is diffracted from the illuminated measurement site at a diffraction order different from a zero diffraction order.

* * * * *